US012655146B2

(12) United States Patent
Bubert et al.

(10) Patent No.: US 12,655,146 B2
(45) Date of Patent: Jun. 16, 2026

(54) PROCESSES FOR THE PREPARATION OF INHIBITORY COMPOUNDS

(71) Applicant: Storm Therapeutics Ltd, Cambridge (GB)

(72) Inventors: Christian Bubert, Oxfordshire (GB); Mark Peter Ridgill, Oxfordshire (GB); Tommaso Canelli, Oxfordshire (GB); David James Hardick, Cambridge (GB)

(73) Assignee: Storm Therapeutics Limited, Cambridge (GB)

( * ) Notice: Subject to any disclaimer, the term of this patent is extended or adjusted under 35 U.S.C. 154(b) by 295 days.

(21) Appl. No.: 18/565,612

(22) PCT Filed: Jun. 1, 2022

(86) PCT No.: PCT/GB2022/051402

§ 371 (c)(1),
(2) Date: Nov. 30, 2023

(87) PCT Pub. No.: WO2022/254218

PCT Pub. Date: Dec. 8, 2022

(65) Prior Publication Data

US 2024/0279222 A1 Aug. 22, 2024

(30) Foreign Application Priority Data

Jun. 2, 2021 (GB) ..................................... 2107905

(51) Int. Cl.
*C07D 471/04* (2006.01)

(52) U.S. Cl.
CPC ................................. *C07D 471/04* (2013.01)

(58) Field of Classification Search
CPC ................................................... C07D 471/04
USPC ......................................................... 544/282
See application file for complete search history.

(56) References Cited

FOREIGN PATENT DOCUMENTS

WO WO-2020/201773 A1 10/2020
WO WO-2021/111124 A1 6/2021

OTHER PUBLICATIONS

International Search Report and Written Opinion for International Application No. PCT/GB22/51402 dated Jul. 27, 2022, 11 pages.

*Primary Examiner* — Kristin A Vajda
(74) *Attorney, Agent, or Firm* — Foley Hoag LLP; David P. Halstead; Alexander J. Chatterley

(57) ABSTRACT

The present invention relates to processes for the preparation of certain compounds that function as inhibitors of METTL3 (N6-adenosine-methyltransferase 70 kDa subunit) activity, and their synthetic intermediates.

22 Claims, No Drawings

PROCESSES FOR THE PREPARATION OF INHIBITORY COMPOUNDS

RELATED APPLICATIONS

This application is a U.S. National Stage filing under 35 U.S.C. § 371 of PCT Application No. PCT/GB22/51402, filed Jun. 1, 2022, which claims priority from United Kingdom Application No. 2107905.8, filed Jun. 2, 2021. The contents of International Patent Application No. PCT/GB22/51402 are incorporated herein by reference in their entirety.

FIELD OF THE INVENTION

The present invention relates to processes for the preparation of certain compounds that function as inhibitors of METTL3 (N6-adenosine-methyltransferase 70 kDa subunit) activity, and their synthetic intermediates.

BACKGROUND OF THE INVENTION

N6-methyladenosine (m6A) is the most common and abundant covalent modification of messenger RNA, modulated by 'writers', 'erasers' and 'readers' of this mark (Meyer & Jaffrey 2014, Niu Y et al, 2013, Yue et al 2015). Approximately 0.1 to 0.5% of all mRNA adenosines are m6A modified (Li Y et al 2015). In vitro data have shown that m6A influences fundamental aspects of mRNA biology, mainly mRNA expression, splicing, stability, localisation and translation (Meyer et al, 2015; Sledz & Jinek 2016). M6A modifications are tissue specific and there is significant variability in their occurrence profiles in non-diseased tissues (eg brain, heart, kidney) and diseased tissues and cells (lung, renal, breast, and leukeamic cancer cells) (Meyer et al 2012).

The m6A modifications and its erasers and writers such as FTO, ALKBH5, methyltransferese like 3 (METTL3) and METTL14 are associated with major diseases such as solid organ cancers, leukaemia, type 2 diabetes, neuropsychiatric behavioural and depressive disorders (Chandola et al 2015; Koranda et al 2018).

The RNA methyltransferase, METTL3, is the major, but not the sole enzyme, that catalyses m6A modification of RNA. It exists as a hetero-trimeric complex with METTLI4 (Liu et al 2014, Wang et al 2016) and Wilm's Tumour Associated Protein (WTAP) (Ping et al 2014). Catalytic activity resides in METTL3, which transfers a methyl group from the co-factor S-adenosyl methionine to the substrate RNA and METTL14 facilitates substrate RNA binding. WTAP localises the complex in specific nuclear regions and also localises RNA substrates to the complex (Wang X et al 2016).

METTL3 has been reported to play a role in many aspects of the development of cancer (Fry et al 2018). Genetic knockdown of METTL3 in lung cancer cell lines (A549, H1299 and H1792) and HeLa cells leads to decreased growth, survival and invasion of human lung cancer cells (Lin S et al 2016). METTL3 is significantly up-regulated in human bladder cancer (Cheng et al 2019). Knockdown of METTL3 drastically reduced bladder cancer cell proliferation, invasion, and survival in vitro and tumorigenicity in vivo. AF4/FMR2 family member 4 (AFF4), two key regulators of NF-κB pathway (IKBKB and RELA) and MYC were further identified as direct targets of METTL3-mediated m6A modification. In renal carcinoma cell lines (CAK-1, CAK-2 and ACHN), genetic knockdown reduced cell proliferation via the phosphatidinylinositol 3-kinase (PI3K)/AKT/mammalian target of rapamycin (mTOR) signalling pathway (Li X et al 2017).

Recently Barbieri et al (2017), defined a set of RNA-modifying enzymes that are necessary for AML leukaemia and identified a key leukaemic pathway for the METTL3 RNA methyltransferase. In this pathway, METTL3 is stably recruited by the CCAAT-box binding transcription factor CEBPZ to promoters of a specific set of active genes, resulting in m6A methylation of the respective mRNAs and increased translation. One important target is SP1, an oncogene in several cancers, which regulates c-MYC expression. Consistent with these findings, it has been reported that METTL3 can methylate its targets co-transcriptionally.

The pathway described by Barbieri et al., is critical for AML leukaemia, as three of its components are required for AML cell growth: (i) the m6A RNA methyltransferase METTL3; (ii) the transcription factor CEBPZ, which targets this enzyme to promoters; and (iii) SP1, whose translation is dependent upon the m6A modification by METTL3. Together, the observations of Barbieri et al define METTL3 enzymatic activity as a new candidate target for the treatment of AML.

In separate, independent studies it has been reported that METTL3 plays an essential role in controlling myeloid differentiation of mammalian normal hematopoietic and leukemic cells (Vu et al 2017). Forced expression of wild type METTL3, but not a mutant METTL3 (with defect in catalytic activity), significantly promotes cell proliferation and inhibits cell differentiation of human cord blood-derived CD34+ haematopoietic stem/progenitor cells (HSPCs). Genetic knockdown of METTL3 has the opposite effects. METTL3 is highly expressed in AML compared to normal HSPCs or other types of cancers. Knockdown of METTL3 in human AML cell lines significantly induces cell differentiation and apoptosis and inhibits leukemia progression in mice xeno-transplanted with MOLM-13 AML cells. The biological function of METTL3 is likely attributed to the promotion of translation of its mRNA targets such as MYC, BCL-2, and PTEN in an m6A-dependent manner.

Recently, METTL3 mediated m6A modification has been demonstrated to play an important role in T cell homeostasis and signal dependent induction of mRNA degradation in CD4 positive T cell lineages (Li et al 2017). Deletion of METTL3 in mouse T cells disrupts T cell homeostasis and differentiation. In a lymphopenic mouse adoptive transfer model, naive Mettl3-deficient T cells failed to undergo homeostatic expansion and remained in the naive state for up to 12 weeks, thereby preventing colitis. Consistent with these observations, the mRNAs of SOCS family genes encoding the STAT signalling inhibitory proteins SOCS1, SOCS3 and CISH were marked by m6A, exhibited slower mRNA decay and showed increased mRNAs and levels of protein expression in Mettl3-deficient naive T cells. This increased SOCS family activity consequently inhibited IL-7-mediated STAT5 activation and T cell homeostatic proliferation and differentiation. Thus METTL3 mediated m6A methylation has important roles for inducible degradation of Socs mRNAs in response to IL-7 signalling in order to reprogram naive T cells for proliferation and differentiation, pointing to a role in auto-immunity.

Recent studies have revealed that depletion of METTL3 leads to alterations in the propagation of diverse viruses (Winkler et al). Following viral infection or stimulation of cells with an inactivated virus, deletion of the m6A 'writer' METTL3 led to an increase in the induction of interferon-stimulated genes. Consequently, propagation of different viruses was suppressed in an interferon-signaling-dependent manner. Significantly, the mRNA of IFNB, was m6A modified and was stabilized following repression of METTL3. m6A serves as a negative regulator of interferon response by dictating the fast turnover of interferon mRNAs and consequently facilitating viral propagation. Therefore METTL3 inhibitors may provide a novel therapeutic approach to a range of infectious and inflammatory diseases.

Improved processes for the manufacture of METTL3 inhibitors are therefore required.

REFERENCES

Barbieri I, Tzelepis K, Pandolfini L, Shi J, Millin-Zambrano G, Robson S C, Aspris D, Migliori V, Bannister A J, Han N, De Braekeleer E, Ponstingl H, Hendrick A, Vakoc C R, Vassiliou G S, Kouzarides T. Nature. 2017 Dec. 7; 552 (7683):126-131.

Chandola U, Das R, Panda B. Brief Funct Genomics. 2015 May; 14(3):169-79.

Cheng M, Gao Q, Wu M, Liang Y, Zhu F, Zhang Y, Zhang X, Li Y, Sheng L, Zhang H, Xiong Q, Yuan Q, Oncogene (2019; e-publication ahead of print).

Fry N J, Law B A, Ilkayeva O R, Carraway K R, Holley C L, Mansfield K D. Oncotarget. 2018 Jul. 27; 9(58):31231-31243.

Koranda J L, Dore L, Shi H, Patel M J, Vaasjo L O, Rao M N, Chen K, Lu Z, Yi Y, Chi W, He C, Zhuang X. Neuron. 2018 July 25; 99(2): 283-292.

Li H B, Tong J, Zhu S, Batista P J, Duffy E E, Zhao J, Bailis W, Cao G, Kroehling L, Chen Y, Wang G, Broughton J P, Chen Y G, Kluger Y, Simon M D, Chang H Y, Yin Z, Flavell R A. Nature. 2017 Aug. 17; 548 (7667):338-342

Li X, Tang J, Huang W, Wang F, Li P, Qin C, Qin Z, Zou Q, Wei J, Hua L, Yang H, Wang Z. Oncotarget. 2017 Oct. 10; 8(56):96103-96116.

Li Y, Wang Y, Zhang Z, Zamudio A V, Zhao J C. RNA. 2015 August; 21(8):1511-8.

Lin S, Choe J, Du P, Triboulet R, Gregory R I. Mol Cell. 2016 May 5; 62(3):335-345.

Liu J, Yue Y, Han D, Wang X, Fu Y, Zhang L, Jia G, Yu M, Lu Z, Deng X, Dai Q, Chen W, He C. Nat Chem Biol. 2014 February; 10(2):93-5.

Meyer K D, Patil D P, Zhou J, Zinoviev A, Skabkin M A, Elemento O, Pestova T A, Qian S B, Jaffrey S R. Cell. 2015 Nov. 5; 163(4): 999-1010.

Meyer K D, Jaffrey S R. Nat Rev Mol Cell Biol. 2014 May; 15(5):313-26.

Meyer K D, Saletore Y, Zumbo P, Elemento 0, Mason C E, Jaffrey S R. Cell. 2012 Jun. 22; 149(7):1635-46.

Niu Y, Zhao X, Wu Y S, Li M M, Wang X J, Yang Y G. Genomics Proteomics Bioinformatics. 2013 February; 11(1):8-17.

Ping X L, Sun B F, Wang L, Xiao W, Yang X, Wang W J, Adhikari S, Shi Y, Lv Y, Chen Y S, Zhao X, Li A, Yang Y, Dahal U, Lou X M, Liu X, Huang J, Yuan W P, Zhu X F, Cheng T, Zhao Y L, Wang X, Rendtlew Danielsen J M, Liu F, Yang Y G. Cell Res. 2014 February; 24(2):177-89.

Śledź P, Jinek M. Elife. 2016 Sep. 14; 5.

Vu L P, Pickering B F, Cheng Y, Zaccara S, Nguyen D, Minuesa G, Chou T, Chow A, Saletore Y, MacKay M, Schulman J, Famulare C, Patel M, Klimek V M, Garrett-Bakelman F E, Melnick A, Carroll M, Mason C E, Jaffrey S R, Kharas M G. Nat Med. 2017 November; 23(11): 1369-1376.

Wang X, Feng J, Xue Y, Guan Z, Zhang D, Liu Z, Gong Z, Wang Q, Huang J, Tang C, Zou T, Yin P. Nature. 2016 Jun. 23; 534(7608):575-8

Wang P, Doxtader K A, Nam Y. Mol Cell. 2016 Jul. 21; 63(2):306-317.

Winkler R, Gillis E, Lasman L, Safra M, Geula S, Soyris C, Nachshon A, Tai-Schmiedel J, Friedman N, Le-Trilling Vu T K, Trilling M, Mandelboim M, Hanna, J H, Schwartz S, Stern-Ginossar N. Nature Immunology (2018, e-publication ahead of print).

Yue Y, Liu J, He C. Genes Dev. 2015 Jul. 1; 29(13):1343-55

An object of this invention is to provide processes for preparing inhibitors of METTL3 activity.

SUMMARY OF THE INVENTION

In general, the present invention provides methods for preparing heterocyclic compounds and their synthetic intermediates, which are useful for the production of therapeutic compounds for use in the inhibition of METTL3.

Process for Preparing Int-7

According to one aspect of the present invention, there is provided a process for preparing a compound of the formula Int-7, Int-7

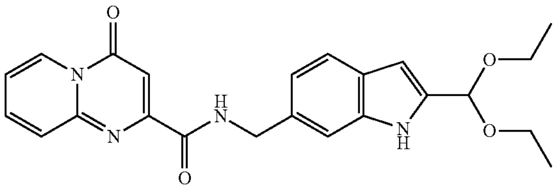

the process comprising reacting a compound of the formula Int-5

Int-5

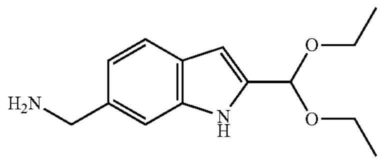

with a compound of the formula Int-6:

Int-6

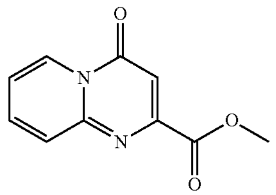

under appropriate reaction conditions.

Compounds Int-5 and Int-6 are suitably reacted in the presence of a suitable solvent. Suitably, the solvent is selected from methanol, THF, dioxane, DMF or dichloromethane. Most suitably, the solvent is methanol.

Suitably, compounds Int-5 and Int-6 are be reacted together in the presence of triethylamine, diisopropylamine, methylamine or pyridine. Most suitably, Int-5 and Int-6 are be reacted together in the presence of triethylamine.

Suitably, the reaction conditions comprise heating compounds Int-5 and Int-6 under reflux conditions.

Suitably, compounds Int-5 and Int-6 are reacted together under amide coupling reaction conditions. Suitable amide coupling conditions may comprise heating compounds Int-5, Int-6 at reflux in methanol in the presence of triethylamine.

Suitably, compounds Int-5 and Int-6 may be made by techniques known in the art using commercially available intermediates as building blocks. The compounds Int-5 and Int-6 may also be made using the method described in the examples section herein.

Conversion of Compound of Formula Int-7 into Compound of Formula VIII

In a preferred embodiment, the process further comprises converting the compound of Int-7 into a compound of Formula VIII below, or a salt or solvate thereof:

VIII

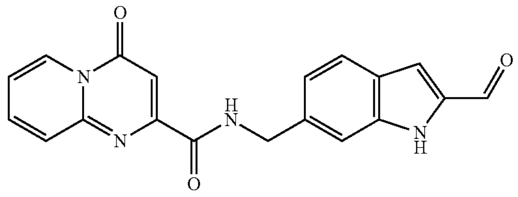

by subjecting the compound of Int-7 to appropriate reaction conditions.

Suitably, converting the compound of Formula Int-7 into a compound of Formula VIII comprises treating the compound of formula of Formula Int-7 with an acid in the presence of a suitable solvent.

The solvent is suitably an aqueous miscible solvent such as THE or dioxane. Most suitably, the solvent is THF.

The acid may be any suitable acid known in the art. Suitably, the acid is selected from hydrochloric acid, trifluoroacetic acid, p-toluenesulfonic acid and acetic acid. Most suitably, the acid is acetic acid.

Suitably, the conversion is carried out at ambient conditions (i.e. room temperature, 20-25° C., and pressure, 1 atm).

Conversion of Compound of Formula VIII into a Compound of Formula I

In an embodiment, the process further comprises converting the compound of Formula VIII into a compound according to Formula I, or a pharmaceutically acceptable salt or solvate thereof:

I

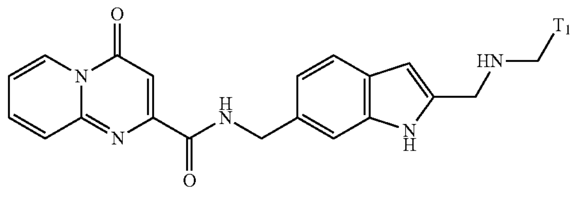

wherein the compound of Formula I is formed by reacting a compound of Formula VIII:

VIII

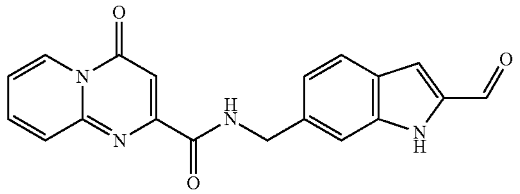

with a compound according to Formula W, or a salt thereof:

W

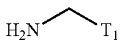

wherein $T_1$ is selected from $C_{1-6}$alkyl, $C_{3-8}$cycloalkyl, aryl, heterocyclyl, heteroaryl, a spirocyclic carbocyclic or heterocyclic ring system, a bridged $C_{3-8}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy.

Suitably, the compound W is in the form of an acid addition salt, e.g. a hydrochloric acid salt, acetate salt, lactic acid salt or maleic acid salt.

Suitably, the compound of Formula W and Formula VIII are reacted together to form an imine intermediate of Formula Int-8:

Int-8

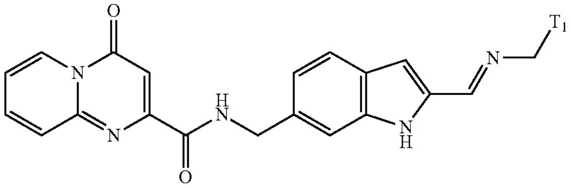

wherein $T_1$ is as defined herein;

and the imine intermediate of Formula Int-8 is subsequently reduced under appropriate reaction conditions to provide the compound of Formula I.

Suitably, the intermediate of Formula Int-8 is formed by reacting the compound of Formula W and Formula VIII together in the presence of triethylamine, diisopropylamine or methylamine in a suitable solvent. Most suitably, the intermdidate of Formula Int-8 is formed by reacting the compound of Formula W and Formula VIII together in the presence of triethylamine.

Suitably, the solvent is selected from dichloromethane, dichloroethane, chloroform or hexafluoroisopropanol. Most suitably, the solvent is dichloromethane.

Suitably, the intermdidate of Formula Int-8 is reduced using a reducing agent in an appropriate solvent. Suitably, the reducing agent is Lithium borohydride or sodium borohydride. Most suitably, the reducing agent is sodium borohydride.

Suitably, the solvent is an alcohol, for example ethanol methanol, isopropanol or n-butanol. Most suitably, the solvent is ethanol Suitably, the compound of Formula I is purified by techniques known in the art, for example by recrystallisation.

Process for Making Compound of Formula I

In a further aspect, there is provided a process for forming a compound according to Formula I, or a pharmaceutically acceptable salt or solvate thereof:

I

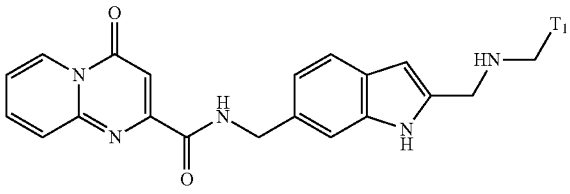

the process comprising reacting a compound of Formula VIII:

VIII

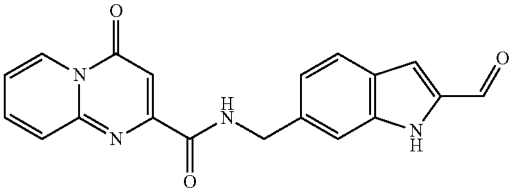

with a compound according to Formula W, or a salt thereof:

W

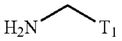

wherein $T_1$ is as defined herein.

Suitably, the compound W is in the form of an acid addition salt, e.g. a hydrochloric acid salt, acetate salt, lactic acid salt or maleic acid salt.

Suitably, the compound of Formula W and Formula VIII are reacted together to form an imine intermediate of Formula Int-8:

Int-8

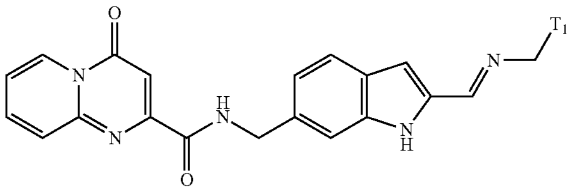

wherein $T_1$ is as defined herein;

and the imine intermediate of Formula Int-8 is subsequently reduced under appropriate reaction conditions to provide the compound of Formula I.

Suitably, the intermdidate of Formula Int-8 is formed by reacting the compound of Formula W and Formula VIII together in the presence of triethylamine, diisopropylamine or methylamine, in a suitable solvent. Most suitably, the intermdidate of Formula Int-8 is formed by reacting the compound of Formula W and Formula VIII together in the presence of triethylamine.

Suitably, the solvent is selected from dichloromethane (DCM), dichloroethane (DCE), chloroform or hexafluoroisopropanol. Most suitably, the solvent is DCM.

Suitably, the intermdidate of Formula Int-8 is reduced using a reducing agent in an appropriate solvent. Suitably, the reducing agent is Lithium borohydride or sodium borohydride. Most suitably, the reducing agent is sodium borohydride.

Suitably, the solvent is an alcohol, for example ethanol methanol, isopropanol or n-butanol. Most suitably, the solvent is ethanol.

Suitably, the compound of Formula I is purified by techniques known to those skilled in the art, for example by recrystallisation. In certain embodiments, $T_1$ is selected from $C_{1-6}$alkyl, $C_{3-6}$cycloalkyl, heterocyclyl, a spirocyclic carbocyclic or heterocyclic ring system, a bridged $C_{3-8}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy.

In certain embodiments, $T_1$ is selected from $C_{3-6}$cycloalkyl, heterocyclyl, a bridged $C_{3-8}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy.

In certain embodiments, $T_1$ is cyclobutyl or a four-membered heterocyclyl, each of which being optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy.

In certain embodiments, $T_1$ is selected from:

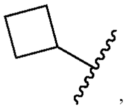 , 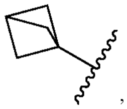 , 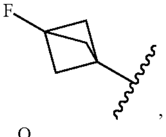 ,

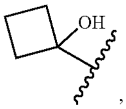 , 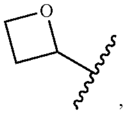 , 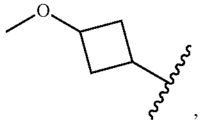 ,

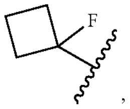 , 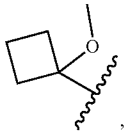 , 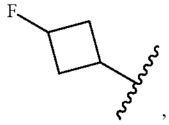 ,

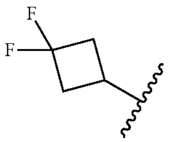 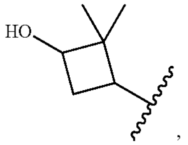 , 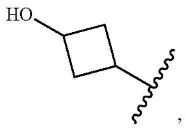 ,

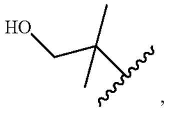 , 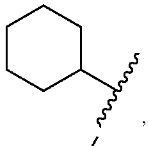 , 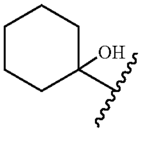 and

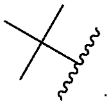 .

In certain preferred embodiments, $T_1$ is cyclobutyl, which may be optionally substituted by one or more methyl, halo, methoxy or hydroxy.

In a preferred embodiment, $T_1$ is cyclobutyl, i.e.

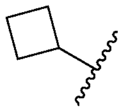 [SMILES: *C1CCC1]

In a preferred embodiment, the compound of Formula I has the structure below, or a pharmaceutically acceptable salt or solvate thereof:

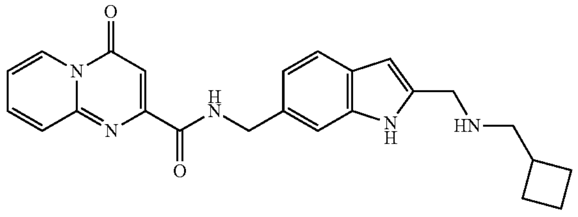 [SMILES: O=C(NCc1ccc2cc(CNCC3CCC3)[nH]c2c1)c1cc(=O)n2ccccc2n1]

DETAILED DESCRIPTION OF THE INVENTION

Definitions

Unless otherwise stated, the following terms used in the specification and claims have the following meanings set out below.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "$C_{1-6}$alkyl" includes $C_{1-4}$alkyl, $C_{1-3}$alkyl, propyl, isopropyl and t-butyl. A similar convention applies to other radicals, for example "phenyl($C_{1-6}$alkyl)" includes phenyl($C_{1-4}$alkyl), benzyl, 1-phenylethyl and 2-phenylethyl.

The term "(m-nC)" or "Cm-n", or "(m-nC) group" or "Cm-n" used alone or as a prefix, refers to any group having m to n carbon atoms.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

An "alkylene" group is an alkyl group that is positioned between and serves to connect two other chemical groups. Thus, "$C_{1-3}$alkylene" means a linear saturated divalent hydrocarbon radical of one to three carbon atoms or a branched saturated divalent hydrocarbon radical of three atoms, for example, methylene, ethylene, propylene, and the like.

The term "$C_{m-n}$cycloalkyl" means a hydrocarbon ring containing from m to n carbon atoms, for example "$C_{3-6}$cycloalkyl" means a hydrocarbon ring containing from 3 to 6 carbon atoms, for example, cyclopropyl, cyclobutyl, cyclopentyl, cyclohexyl. The term "$C_{m-n}$cycloalkyl" also encompasses non-aromatic saturated or partially saturated monocyclic, fused, bridged, or spiro bicyclic carbocyclic ring system(s). The term "$C_{m-n}$cycloalkyl" includes both monovalent species and divalent species. Monocyclic "$C_{m-n}$cycloalkyl" rings contain from about 3 to 12 (suitably from 3 to 8, most suitably from 5 to 6) ring carbon atoms. Bicyclic "$C_{m-n}$cycloalkyl" contain from 7 to 17 ring carbon atoms, suitably 7 to 12 ring carbon atoms. Bicyclic "$C_{m-n}$cycloalkyl" rings may be fused, spiro, or bridged ring systems.

The term "cycloalkoxy" means a cycloalkyl-O-group in which the cycloalkyl group is as previously defined, for example $C_{3-4}$cycloalkoxy (or —O—$C_{3-4}$cycloalkyl) means a hydrocarbon ring containing from 3 to 4 carbon atoms, linked to an O atom e.g.

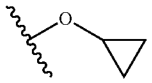
and
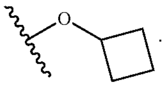
.

The term "halo" or "halogeno" refers to fluoro, chloro, bromo and iodo.

The term "heterocyclyl", "heterocyclic" or "heterocycle" means a non-aromatic saturated or partially saturated monocyclic, fused, bridged, or spiro bicyclic heterocyclic ring system(s). The term heterocyclyl includes both monovalent species and divalent species. Monocyclic heterocyclic rings contain from about 3 to 12 (suitably from 3 to 7, most suitably from 5 to 6) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocycles contain from about 7 to about 17 ring atoms, suitably from 7 to 12 ring atoms. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (═O) or thioxo (═S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

A "carbon-linked heterocyclyl" means a heretocycle group as defined above that is connected via a carbon atom, rather than a heteroatom such as nitrogen.

By "spirocyclic ring systems" it is meant a compound which at least two rings which have only one atom in common and are not linked by a bridge.

By "fused ring systems" it is meant a compound in which two rings share two adjacent atoms. In other words, the rings share one covalent bond.

By "bridged ring systems" is meant ring systems in which two rings share more than two atoms, see for example *Advanced Organic Chemistry*, by Jerry March, 4$^{th}$ Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane and quinuclidine.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members.

The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydro-pyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:

- a benzene ring fused to a 5- or 6-membered ring containing 1, 2 or 3 ring heteroatoms;
- a pyridine ring fused to a 5- or 6-membered ring containing 1, 2 or 3 ring heteroatoms;
- a pyrimidine ring fused to a 5- or 6-membered ring containing 1 or 2 ring heteroatoms;
- a pyrrole ring fused to a 5- or 6-membered ring containing 1, 2 or 3 ring heteroatoms;
- a pyrazole ring fused to a 5- or 6-membered ring containing 1 or 2 ring heteroatoms;
- a pyrazine ring fused to a 5- or 6-membered ring containing 1 or 2 ring heteroatoms;
- an imidazole ring fused to a 5- or 6-membered ring containing 1 or 2 ring heteroatoms;
- an oxazole ring fused to a 5- or 6-membered ring containing 1 or 2 ring heteroatoms;
- an isoxazole ring fused to a 5- or 6-membered ring containing 1 or 2 ring heteroatoms;
- a thiazole ring fused to a 5- or 6-membered ring containing 1 or 2 ring heteroatoms;
- an isothiazole ring fused to a 5- or 6-membered ring containing 1 or 2 ring heteroatoms;
- a thiophene ring fused to a 5- or 6-membered ring containing 1, 2 or 3 ring heteroatoms;
- a furan ring fused to a 5- or 6-membered ring containing 1, 2 or 3 ring heteroatoms;
- a cyclohexyl ring fused to a 5- or 6-membered heteroaromatic ring containing 1, 2 or 3 ring heteroatoms; and
- a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzfuranyl, benzthiophenyl, benzimidazolyl, benzoxazolyl, benzisoxazolyl, benzthiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

The term “aryl” means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In particular embodiment, an aryl is phenyl.

The term “optionally substituted” refers to either groups, structures, or molecules that are substituted and those that are not substituted.

Where optional substituents are chosen from “one or more” groups it is to be understood that this definition includes all substituents being chosen from one of the specified groups or the substituents being chosen from two or more of the specified groups.

Suitably, a heteroaryl or heterocyclyl group as defined herein is a monocyclic heteroaryl or heterocyclyl group comprising one, two or three heteroatoms selected from N, O or S.

Suitably, a heteroaryl is a 5- or 6-membered aryl or heteroaryl ring comprising one, two or three heteroatoms selected from N, O or S.

Suitably, a heterocyclyl group is a 4-, 5- or 6-membered heterocyclyl ring comprising one, two or three heteroatoms selected from N, O or S. Most suitably, a heterocyclyl group is a 5- or 6-membered ring comprising one, two or three heteroatoms selected from N, O or S [e.g. morpholinyl (e.g. 4-morpholinyl), oxetane, methyloxetane (e.g. 3-methyloxetane), pyrrolidinone (e.g. pyrrolidin-2-one)].

Suitably, an aryl group is phenyl.

It is to be understood that certain compounds and intermediates disclosed herein may exist in salt forms. A suitable pharmaceutically acceptable salt of a compound of Formula I is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of a compound disclosed herein which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, trimethylamine, piperidine, morpholine or tris-(2-hydroxyethyl)amine.

It is also to be understood that certain compounds disclosed herein may exist in solvated as well as unsolvated forms such as, for example, hydrated forms.

EXAMPLES

The example and preparations provided below further illustrate and exemplify the compounds of the present invention and methods of preparing such compounds. It is to be understood that the scope of the present invention is not limited in any way by the scope of the following examples and preparations. Persons skilled in the art will recognize that the chemical reactions described may be readily adapted to prepare a number of other METTL3 inhibitors, and alternative methods for preparing such compounds are deemed to be within the scope of this invention. For example, the synthesis of non-exemplified compounds according to Formula I may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

Chemical Synthesis

An overview of the process to form a compound according Formula I is provided in Scheme 1 below:

Scheme 1 - Overview of Process for forming compound of Formula (I)
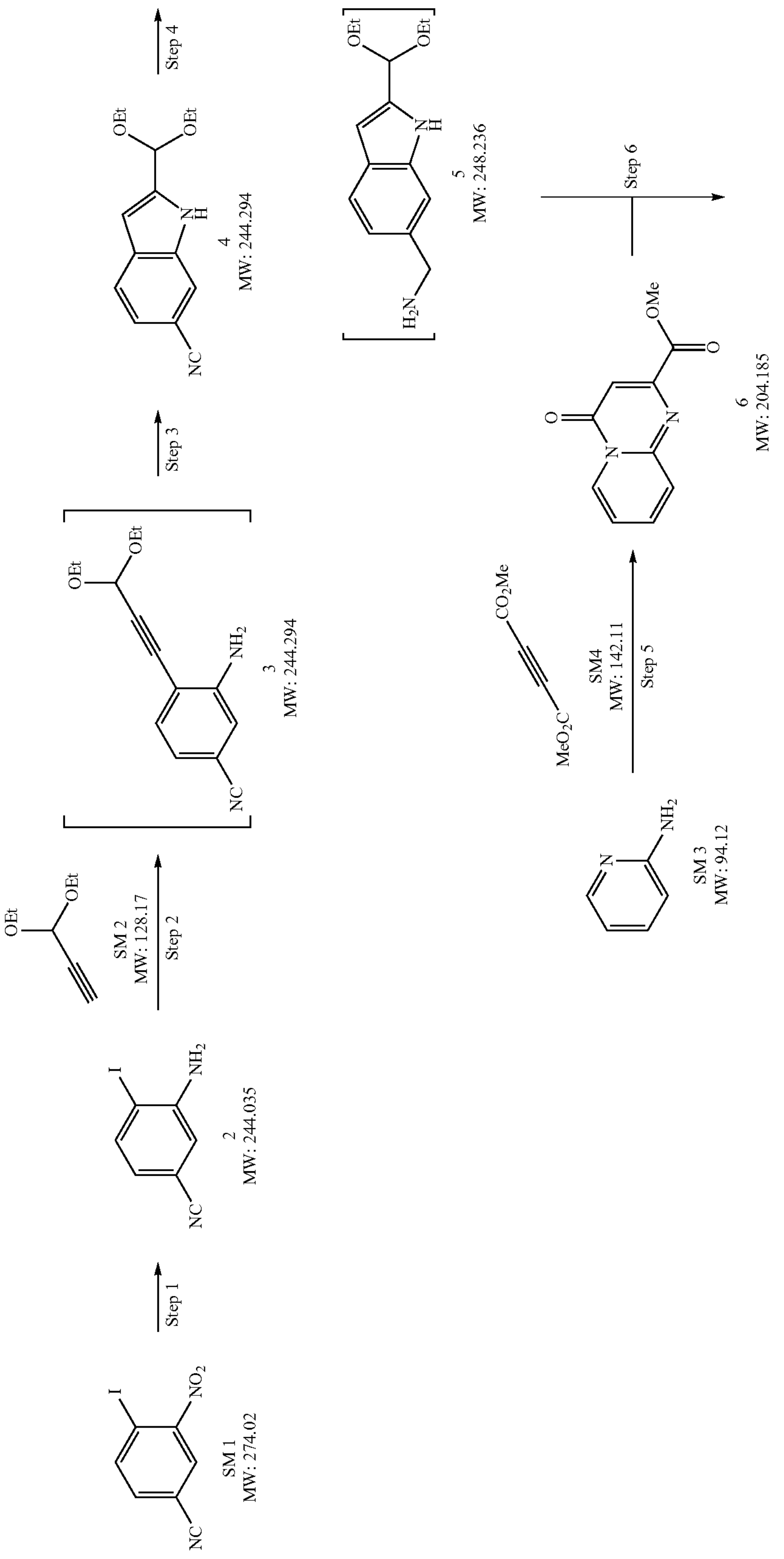

-continued
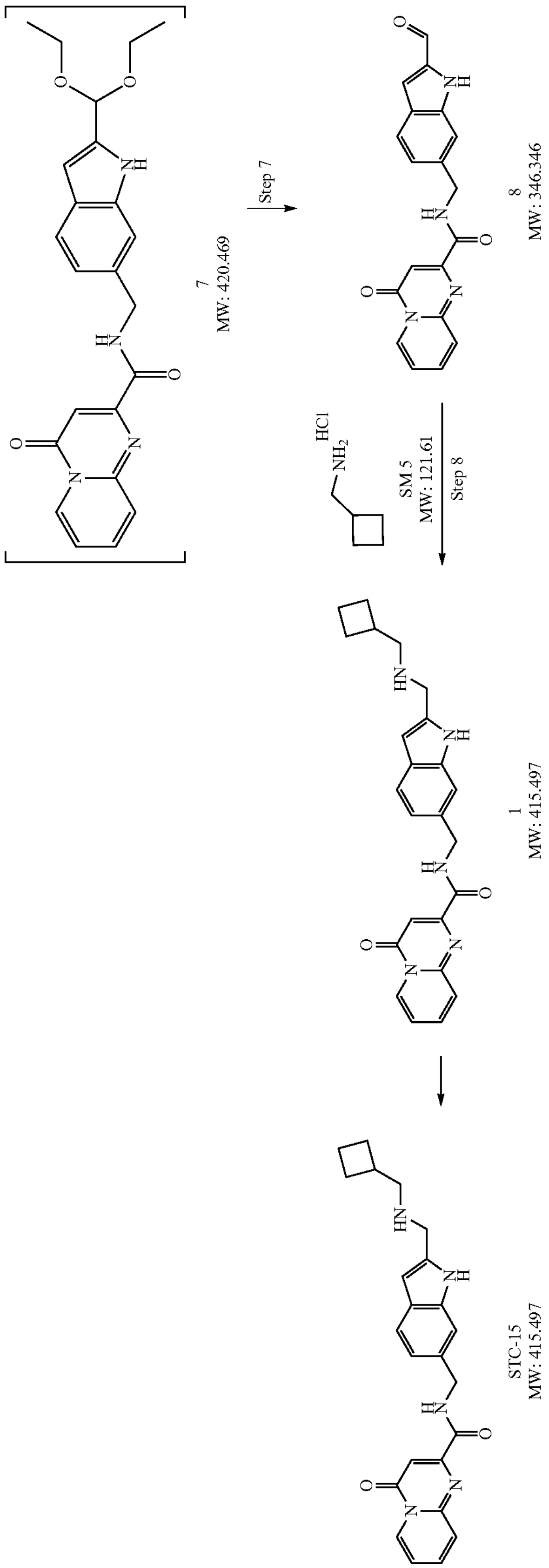
7
MW: 420.469
8
MW: 346.346
1
MW: 415.497
STC-15
MW: 415.497

3-Amino-4-iodobenzonitrile (2)

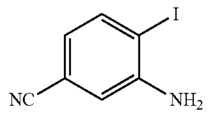

4-Iodo-3-nitrobenzonitrile (50 g, 0.18 mol, 1 eq.) was dissolved in THE (375 ml) to give a yellow solution. In a 1 L jacketed reactor, sodium dithionite (135 g, 0.69 mol, 3.8 eq) was suspended in water and the mixture was stirred at 20° C. The solution of 4-iodo-3-nitrobenzonitrile in THE was charged to the reactor over 2 h maintaining the temperature below 25° C. The mixture was stirred for 4 hours, then the stirring was stopped and the organic phase was removed. The aqueous layer was washed with THE (100 ml) and the combined organic phases were charged to the vessel. Aq. HCl 37% w/w (100 ml) was added dropwise over 1 hour and the resulting suspension was stirred for 18 hours. The temperature was decreased to 10° C. and the mixture was basified by the dropwise addition of aq. NaOH 5 M (235 ml) and aq. $Na_2CO_3$ 10% w/w (25 ml). The temperature was increased to 20° C. and the mixture was stirred for 20 minutes. Then stirring was stopped and the phases were separated. The organic phase was concentrated to 150 ml under reduced pressure and IPA (500 ml) was added. The mixture was concentrated under vacuum to a total of 150 ml and it was heated to reflux. Then it was cooled to 40° C. and water (500 ml) was added. The slurry was aged for 10 minutes at 40° C. and then the temperature was decreased to 20° C. over 1 hour. The suspension was aged for 16 hours and it was filtered. The wet cake was washed with water (2×100 ml). The wet solid was dried for 6 hours at 45° C. under vacuum to give 33 g (74% mol yield) of 3-amino-4-iodobenzonitrile as yellow solid (33 g, 0.135 mol, 74% mol yield).

HPLC: 99.5% purity (220 nm).

1H NMR (400 MHz, DMSO-d6): 5.72 (s, 2H), 6.68 (dd, 1H), 7.02 (d, 1H), 7.76 (d, 1H). UPLC-MS: $[M+H]^+$ 244.93.

2-(Diethoxymethyl)-1H-indole-6-carbonitrile (4)

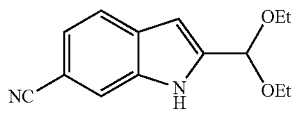 [SMILES: CCOC(OCC)c1cc2ccc(C#N)cc2[nH]1]

3-Amino-4-iodobenzonitrile (930 g, 3.81 mol, 1 eq.) was dissolved in 2-MeTHF (9.1 L) in a 20 L jacketed reactor, followed by the addition of $PdCl_2(PPh_3)_2$ (26.7 g, 0.01 eq.), triphenylphosphine (20 g, 0.02 eq.), copper (I) iodide (14.5 g, 0.02 eq.) and triethylamine (1.59 L, 3 eq.). The mixture was stirred at 20° C. and three nitrogen-vacuum cycles were performed. Then 3,3-diethoxyprop-1-yne (656 ml, 1.2 eq.) was added over twenty minutes and the reaction mixture was stirred at 20° C. under a nitrogen atmosphere for 18 hours ° C. The mixture was filtered to remove insoluble salts. The wet cake was washed with 2-MeTHF (2×2.8 L) and the washes and the filtrate were combined and charged to the reactor. The temperature was raised to 40° C. and the solution was concentrated under vacuum to a total of 10.2 L. The mixture was cooled to 30° C. and it was sequentially washed with aq. 10% w/w $NH_3$ (2×9.3 L), aq. 13% w/w NaCl (1×9.3 L), aq. 10% w/w sodium bisulfite (2×9.3 L) and aq. 13% w/w NaCl (1×9.3 L, 1×10 vol). The organic layer was filtered through an active charcoal CUNO cartridge and the CUNO cartridge was washed with 2-MeTHF (7.4 L). The filtrate and the washes were combined and charged to the reactor. The temperature was raised to 100° C. and the mixture was concentrated at reflux to a total of 2.8 L. The temperature was decreased to 25° C. and the mixture was sampled to monitor the residual water content. LiHMDS 1 M in THE (7.6 L, 2 eq.) was charged to the vessel dropwise over 40 minutes keeping the internal temperature below 30° C. The solution was heated to reflux (75° C.) and it was stirred for 4 hours. The temperature was decreased to 10° C. and aq. 20% w/w $NH_4Cl$ (9.3 L) was added dropwise over 1 hour keeping the temperature below 25° C. The mixture was warmed to 20° C. and it was stirred for 30 minutes. Stirring was stopped and the aqueous layer was removed. The organic phase was filtered through a celite pad (465 g). The pad was washed with 2-MeTHF (7.5 L). The filtrate and the washes were combined and poured in the reactor. The mixture was concentrated under vacuum to 1.9 L and it was diluted with DCM to 6.5 L. The mixture was concentrated under vacuum to 1.9 L and it was diluted with DCM to 2.6 L. The temperature was decreased to 20° C. and crude product was absorbed on a silica pad (2.8 kg). The pad was eluted with cyclohexane (4.7 L) and cyclohexane/EtOAc 1/1 (11.2 L). The eluted solvents containing the desired product were charged to the reactor and concentrated under vacuum to a total of 2 L. Then DCM was charged to a total of 6.5 L. The mixture was concentrated under vacuum to 2.8 L. Then DCM was charged to 7.4 L. The mixture was concentrated under vacuum to a total of 2.8 L. The temperature was decreased to 20° C. and heptane (13 L) was added dropwise to the mixture over 1.5 hours. The mixture was stirred at 20° C. for 16 hours then it was cooled to 0° C. over 2 hours and stirred at 0° C. for 2 hours. The slurry was then filtered. The wet cake was washed with heptane (2×1.9 L). The wet solid was dried under vacuum at 45° C. for 16 hours to give 2-(diethoxymethyl)-1H-indole-6-carbonitrile as brown solid (562 g, 2.3 mol, 60% mol yield).

HPLC: 99.9% purity (220 nm).

1H NMR (400 MHz, DMSO-d6): 1.19 (t, 6H), 3.59 (m, 4H), 5.77 (s, 1H), 6.56 (s, 1H), 7.32 (dd, 1H), 7.69 (d, 1H), 7.80 (m, 1H), 11.68 (s, 1H). UPLC-MS: $[M-H]^-$ 243.19.

Methyl 4-oxo-4H-pyrido[1,2-a]pyrimidine-2-carboxylate (6)

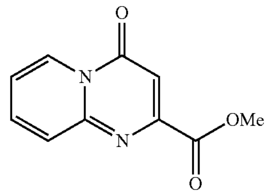 [SMILES: COC(=O)c1cc(=O)n2ccccc2n1]

In a 20 L glass jacketed reactor, pyridin-2-amine (350 g, 3.8 mol, 1.0 eq.) followed by 17.5 L of water were charged and stirred at 20° C. for 10 minutes until complete dissolution was achieved. Then $NaHCO_3$ (781 g, 2.5 eq.) was charged to the vessel and the mixture was stirred until a solution was observed. 1,4-Dimethyl but-2-ynedioate (550 mL, 1.2 eq.) was charged dropwise in the vessel over 2h.

The red/brown mixture was stirred at 20° C. for 1 hour. After 2 h the reaction mixture was extracted with DCM (2×3.5L). The organic layers were stored in a tank and the reactor was cleaned. Additional pyridin-2-amine (100 g, 1.0 mol, 1.0 eq.) was charged to the vessel and the reaction and the workup were repeated as described herein. The organic phases from the two runs were combined and washed with 2.25 L of water. The aqueous layer was removed and the organic layer was concentrated to 0.9 L under vacuum. Then ethyl acetate (2.25 L) was charged and the mixture was concentrated to 2.7 L. The resulting suspension was stirred at 20° C. for 14 h and filtered. The wet cake was washed with of EtOAc/n-heptane 1/1 (1×1.4 L) and with n-heptane (1×0.5 L). The wet solid was dried under vacuum at 45° C. for 4 h to give methyl 4-oxo-4H-pyrido[1,2-a]pyrimidine-2-carboxylate as a brown solid (533 g, 2.6 mol, 55% mol yield). HPLC: 98.6% purity (220 nm). 1H NMR (400 MHz, DMSO-d6): 3.91 (s, 4H), 6.91 (s, 1H), 7.48 (td, 1H), 7.87 (dt, 1H), 8.08 (ddd, 1H), 9.01 (d, 1H). UPLC-MS: $[M+H]^+$ 205.04.

N-[(2-formyl-1H-indol-6-yl)methyl]-4-oxo-4H-pyrido[1,2-a]pyrimidine-2-carboxamide (8)

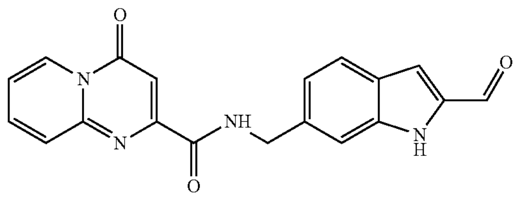 [SMILES: O=Cc1cc2ccc(CNC(=O)c3cc(=O)n4ccccc4n3)cc2[nH]1]

2-(Diethoxymethyl)-1H-indole-6-carbonitrile (555 g, 2.27 mol, 1 eq.), was charged to a 20 L Buchi hydrogenator vessel followed by MeOH (5.6 L), Raney-Ni 50% w/w suspension in water (227 g, 0.4 wt dry base) and $NH_3$ 7 M in MeOH (2.2 L). The reactor was sealed and the jacket temperature was raised to 50° C. The mixture was stirred at 50° C. under 10 bar hydrogen pressure for 3 hours. The mixture was cooled to 20° C. and filtered to remove the catalyst. The filter and the line were washed with MeOH (4.4 L). The filtrate and the washes were combined and charged to a 20 L jacketed reactor. The solution was concentrated at reflux at atmospheric pressure to a total of 4.4 L. The temperature was decreased to 45° C. and the mixture was concentrated under vacuum to a total of 1.7 L. The mixture was diluted with MeOH (5.6 L) and concentrated under vacuum to a total of (1.7 L). The mixture was diluted with MeOH (3.3 L) and cooled to 20° C. Methyl 4-oxo-4H-pyrido[1,2-a]pyrimidine-2-carboxylate (510 g, 1.1 eq.) and triethylamine (475 ml, 1.5 eq.) were charged to the vessel.

The resulting suspension was heated to reflux and stirred for 16 hours. The mixture was concentrated at atmospheric pressure to a total of 3 L. The temperature was decreased to 40° C. and the mixture was concentrated under vacuum to a total of (1.7 L). The mixture was cooled to 20° C. and it was diluted with THE to a total of 5.6 L. The temperature was decreased to 5° C. and then NaOH 0.4 M aqueous (5.6 L) was added dropwise to the mixture over 1.5 hours keeping the internal temperature below 25° C. The temperature was increased to 20° C. and the mixture was stirred for 1.5 hours. The temperature was decreased to 10° C. and acetic acid (1.1 L) was added dropwise to the reaction mixture over 30 minutes keeping the internal temperature below 20° C. The mixture was stirred at 20° C. for 16 hours. Water (11.1 L) was added dropwise to the reaction mixture over 45 minutes and the slurry was aged at 20° C. for 16 hours. The suspension was filtered and the wet cake was washed with water (2×1.7 L). The wet solid was dried under vacuum at 50° C. for 48 hours to give 600 g of N-[(2-formyl-1H-indol-6-yl)methyl]-4-oxo-4H-pyrido[1,2-a]pyrimidine-2-carboxamide as a brown solid, with 12 mol % residual amount N-{[2-(diethoxymethyl)-1H-indol-6-yl]methyl}-4-oxo-4H-pyrido[1,2-a]pyrimidine-2-carboxamide.

N-[(2-formyl-1H-indol-6-yl)methyl]-4-oxo-4H-pyrido[1,2-a]pyrimidine-2-carboxamide (600 g) was charged to a 20 L jacketed reactor at 20° C. followed by NMP (2.4 L). The mixture was stirred for 20 minutes and aqueous HCl 2 M (600 mL) was added dropwise over 15 minutes. The mixture was stirred for 2 hours and aqueous NaOH 1 M (1.2 L) was added over 45 minutes. The mixture was diluted with water (7.2 L) and stirred at 20° C. for 16 hours. The slurry was filtered and the wet cake was washed with water (2×1.7 L). The wet solid was dried under vacuum for 72 hours to give N-[(2-formyl-1H-indol-6-yl)methyl]-4-oxo-4H-pyrido[1,2-a]pyrimidine-2-carboxamide as brown solid (556 g, 1.61 mol, 70% mol yield). HPLC: 99.4% purity (240 nm). 1H NMR (400 MHz, DMSO-d6): 4.61 (d, 2H), 6.91 (s, 1H), 7.14 (dd, 1H), 7.37 (m, 1H), 7.45 (m, 2H), 7.70 (d, 1H), 7.78 (d, 1H), 8.08 (ddd, 1H), 9.03 (d, 1H), 9.43 (t, 1H), 9.81 (s, 1H), 11.92 (s, 1H). UPLC-MS: $[M+H]^+$ 347.15.

N-[(2-{[(cyclobutylmethyl)amino]methyl)-1H-indol-6-yl)methyl]-4-oxo-4H-pyrido[1,2-a]pyrimidine-2-carboxamide (1)

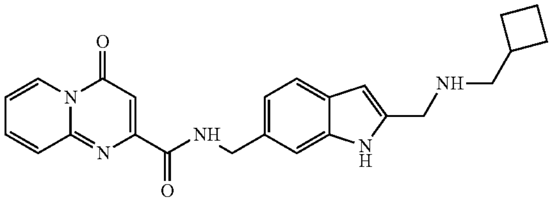 [SMILES: O=C(NCc1ccc2cc(CNCC3CCC3)[nH]c2c1)c1cc(=O)n2ccccc2n1]

In a 20 L jacketed reactor, cyclobutylmethanamine HCl (233 g, 1.2 eq.) was suspended in DCM (5.5 L), followed by the addition of triethylamine (335 ml, 1.5 eq.) at 20° C. The mixture was stirred at 20° C. for 10 minutes and N-[(2-formyl-1H-indol-6-yl)methyl]-4-oxo-4H-pyrido[1,2-a]pyrimidine-2-carboxamide (554 g, 1.60 mol, 1 eq.) was charged. The resulting suspension was stirred at 20° C. for 3.5 hours. The reaction was then filtered through an in line 5 μm Sartorius filter. The line and the filters were washed with DCM (1.4 L). The filtrate and the washes were charged to the reactor and concentrated under vacuum to a total of (4.2 L). The temperature was decreased to 20° C. and the mixture was diluted with DCM to a total of 6.1 L. The solution of imine intermediate in DCM was discharged to a tank and it was stored at 20° C. The reactor was cleaned between batches with DCM and absolute EtOH. Then, in the vessel a suspension of $NaBH_4$ (133 g, 2.2 eq.) in abs. EtOH (6.9 L) was prepared and cooled to 0° C. The solution of the imine in DCM was added dropwise to the $NaBH_4$ suspension over 1 hour and 45 minutes keeping the temperature below 5° C. The reaction mixture was stirred for 30 minutes at 0° C. and EtOH/water 8/2 (1.1 L) was added dropwise over 30 minutes keeping the temperature below 5° C. Then water (2.5 L) was added dropwise over 1.5 hours keeping the temperature below 5° C. Precipitation of a solid and phase splitting observed. The mixture was filtered and the wet cake was washed with DCM/EtOH 1/1 (2×1.7 L). The filtrate and the washes were charged to the reactor and the mixture (biphasic solution) was stirred at 20° C. Water (2.8 L) was added dropwise over 20 minutes and the mixture was stirred for a further 20 minutes. Stirring was stopped and the phases were left to split for 40 minutes. The aqueous phase was removed and the organic phase was filtered through an active charcoal CUNO cartridge. The cartridge was washed with DCM/EtOH 1/1 (5.5 L). The filtrate and the washes were charged to the vessel and the mixture was concentrated under vacuum to a total of 2.8 L. Ethanol (1.1 L) was then charged. The slurry was aged at 40° C. for 30 minutes and then the temperature was decreased to 20° C. over 1 hour. The mixture was aged at 20° C. for two hours and it was filtered. The wet cake was washed with EtOH (2×1.7 L). The wet solid was dried under vacuum at 45° C. for 16 hours to give N-[(2-{[(cyclobutylmethyl)amino]methyl)-1H-indol-6-yl)methyl]-4-oxo-4H-pyrido[1,2-a]pyrimidine-2-carboxamide as brown solid (430 g, 1.03 mol, 65% mol yield).

HPLC: 95.6% purity (240 nm).

1H NMR (400 MHz, DMSO-d6): 1.60 (m, 2H), 1.70-2.05 (m, 5H), 2.40 (m, 1H), 3.77 (s, 2H), 4.57 (d, 2H), 6.20 (m, 1H), 6.91 (s, 1H), 6.97 (dd, 1H), 7.31 (s, 1H), 7.37 (d, 1H), 7.44 (td, 1H), 7.77 (m, 1H), 8.05 (ddd, 1H), 9.01 (d, 1H), 9.21 (t, 1H), 10.86 (s, 1H). UPLC-MS: $[M+H]^+$ 416.32.

The invention claimed is:

1. A process for preparing a compound of the formula Int-7, or a salt or solvate thereof:

Int-7

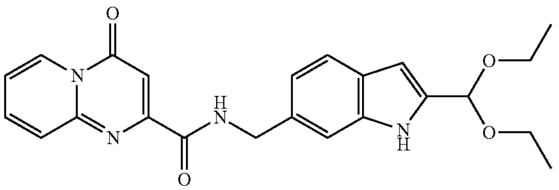

the process comprising reacting a compound of the formula Int-5

Int-5

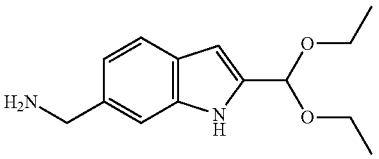

with a compound of the formula Int-6:

Int-6

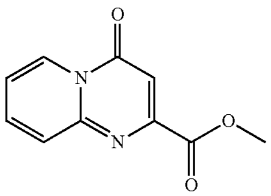

under appropriate reaction conditions.

2. The process of claim 1, wherein compounds Int-5 and Int-6 are reacted together in the presence of a suitable solvent.

3. The process of claim 1, wherein compounds of Formulas Int-5 and Int-6 are reacted together in the presence of triethylamine, diisopropylamine, methylamine or pyridine.

4. The process of claim 1, wherein the compound of Formula Int-5 and of Formula Int-6 are reacted together under reflux conditions.

5. The process of claim 1, further comprising converting the compound of Formula Int-7 into a compound of Formula VIII below, or a salt or solvate thereof:

VIII

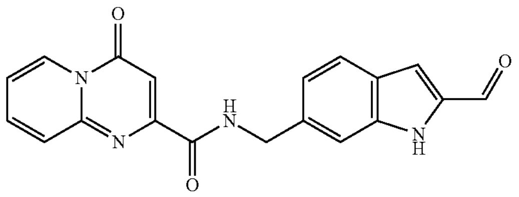

by subjecting the compound of Formula Int-7 to appropriate reaction conditions.

6. The process of claim 5, wherein the step of converting comprises treating the compound of formula Int-7 with an acid in the presence of a suitable solvent.

7. The process of claim 6, wherein the acid is selected from HCl, trifluoroacetic acid, p-toluenesulfonic acid and acetic acid.

8. The process of claim 5, further comprising converting the compound of Formula VIII into a compound according to Formula I below, or a pharmaceutically acceptable salt or solvate thereof:

I

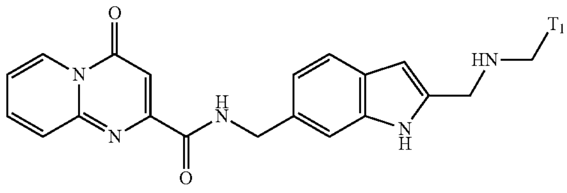

wherein the compound of Formula I is formed by reacting a compound of Formula VIII:

VIII

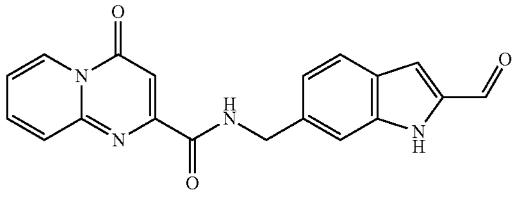

with a compound according to Formula W, or a salt thereof:

W

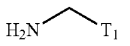

wherein $T_1$ is selected from $C_{1-6}$alkyl, $C_{3-8}$cycloalkyl, aryl, heterocyclyl, heteroaryl, a spirocyclic carbocyclic or heterocyclic ring system, a bridged $C_{3-8}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy.

9. The process of claim 8, wherein the compound of Formula W is in the form of a hydrochloric acid salt, acetate salt, lactic acid salt or maleic acid salt.

10. The process of claim 8, wherein the compound of Formula W and Formula VIII are reacted together in the presence of triethylamine, diisopropylamine or methylamine in a suitable solvent to form an imine intermediate of Formula Int-8:

Int-8

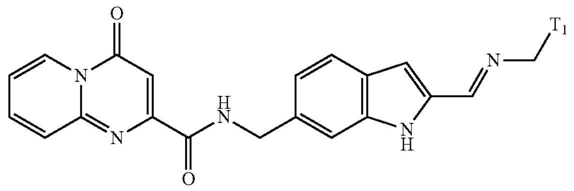

wherein $T_1$ is selected from $C_{1-6}$alkyl, $C_{3-8}$cycloalkyl, aryl, heterocyclyl, heteroaryl, a spirocyclic carbocyclic or heterocyclic ring system, a bridged $C_{3-8}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy;

and Int-8 is subsequently reduced using a reducing agent in an appropriate solvent to provide the compound of Formula I.

11. The process of claim 10, wherein the reducing agent is lithium borohydride or sodium borohydride.

12. A process for forming a compound according to Formula I, or a pharmaceutically acceptable salt or solvate thereof:

I

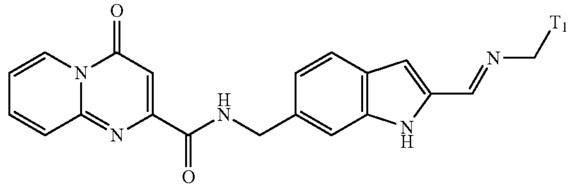

the process comprising reacting a compound of Formula VIII:

VIII

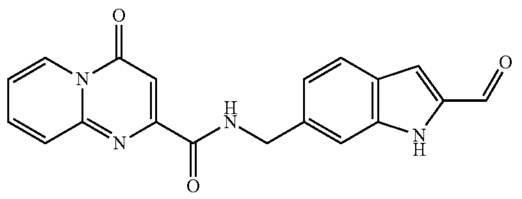

with a compound according to Formula W, or a salt thereof:

W

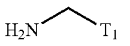

wherein $T_1$ is selected from $C_{1-6}$alkyl, $C_{3-8}$cycloalkyl, aryl, heterocyclyl, heteroaryl, a spirocyclic carbocyclic or heterocyclic ring system, a bridged $C_{3-8}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy.

13. The process of claim 12, wherein the compound of Formula W is in the form of a hydrochloric acid salt, acetate salt, lactic acid salt or maleic acid salt.

14. The process of claim 12, wherein the compound of Formula W and Formula VIII are reacted together in the presence of triethylamine, diisopropylamine or methylamine in a suitable solvent to form an imine intermediate of Formula Int-8:

Int-8

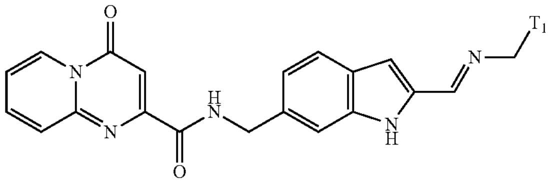

wherein $T_1$ is as defined in claim 12;

and Int-8 is subsequently reduced using a reducing agent in an appropriate solvent to provide the compound of Formula I.

15. The process of claim 14, wherein the reducing agent is lithium borohydride or sodium borohydride.

16. The process according claim 8, wherein $T_1$ is selected from $C_{1-6}$alkyl, $C_{3-6}$cycloalkyl, heterocyclyl, a spirocyclic carbocyclic or heterocyclic ring system, a bridged $C_{3-8}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo or $C_{1-2}$-haloalkoxy.

17. The process according to claim 8, wherein $T_1$ is selected from $C_{3-6}$cycloalkyl, heterocyclyl, a bridged $C_{3-8}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy.

18. The process according to claim 8, wherein $T_1$ is cyclobutyl or a four-membered heterocyclyl, each of which being optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy.

19. The process according to claim 8, wherein $T_1$ is selected from:

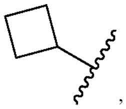,
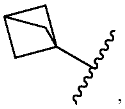,
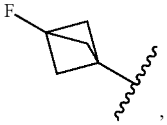,
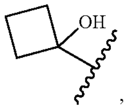,
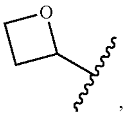,
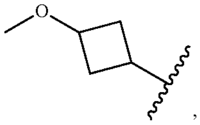,
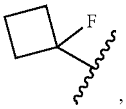,
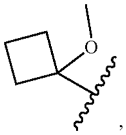,
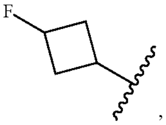, -continued

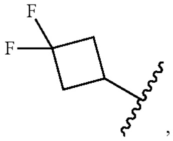,
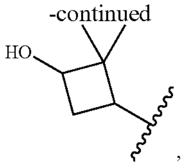,
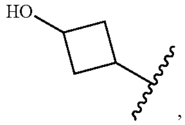,
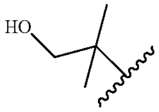,
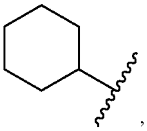,
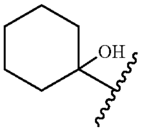
and
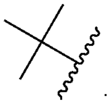.

20. The process according to claim 8, wherein $T_1$ is cyclobutyl.

21. The process according to claim 2, wherein the solvent is methanol, THF, dioxane, DMF or dichloromethane.

22. The process according to claim 6, wherein the solvent is THF or dioxane.

* * * * *